United States Patent

Süling et al.

[11] Patent Number: 5,892,081
[45] Date of Patent: Apr. 6, 1999

[54] SELECTIVE PREPARATION OF RACEMIC ANSA-METALLOCENE COMPLEXES

[75] Inventors: Carsten Süling, Frankenthal; Mario Huettenhofer, Constance, both of Germany; Hans-Herbert Brintzinger, Taegerswilen, Switzerland; Frank Schaper, Constance, Germany

[73] Assignee: BASF Aktiengesellschaft, Ludwigshafen, Germany

[21] Appl. No.: 114,190

[22] Filed: Jul. 13, 1998

[30] Foreign Application Priority Data

Jul. 18, 1997 [DE] Germany ......................... 197 30 880.5

[51] Int. Cl.$^6$ ..................................... C07F 17/00
[52] U.S. Cl. ................... 556/28; 556/7; 556/11; 556/12; 556/21; 556/43; 556/53; 556/87; 556/95; 502/103; 502/117; 502/153; 526/160; 526/943
[58] Field of Search ................... 556/95, 87, 11, 556/12, 43, 53, 7, 21, 28; 502/103, 117, 153; 526/160, 943

[56] References Cited

U.S. PATENT DOCUMENTS 5,474,716 12/1995 Lisowsky ............................. 260/665 G
5,543,535 8/1996 Lisowsky ................................. 556/11

FOREIGN PATENT DOCUMENTS

92/09545 6/1992 WIPO .

OTHER PUBLICATIONS

J. Am. Chem. Soc. 1990, 112, 4911–4914, Waymouth et al.
J. Am. Chem. Soc. 1991, 113, 6270–6271, Coates et al.
Organometallics 1992, 1869–1876, Rheingold et al.

Primary Examiner—Porfirio Nazario-Gonzalez
Attorney, Agent, or Firm—Keil & Weinkauf

[57] ABSTRACT

The present invention relates to a process for preparing racemic ansa-metallocene complexes I

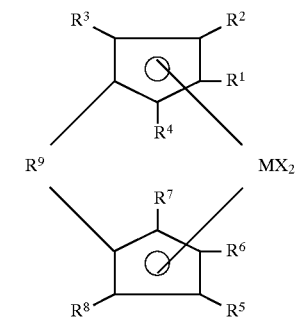

tin compounds II

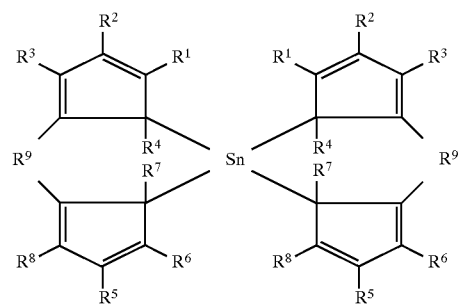

and a process for preparing tin compounds II. $R^1$ to $R^9$, M, and X are defined herein.

9 Claims, No Drawings

SELECTIVE PREPARATION OF RACEMIC ANSA-METALLOCENE COMPLEXES

The present invention relates to a process for preparing racemic ansa-metallocene complexes I as defined herein, tin compounds II as described herein and a process for preparing tin compounds II, as also defined herein.

Apart from stereospecific olefin polymerization, enantioselective organic synthesis is increasingly providing interesting opportunities for using chiral ansa-metallocene complexes of metals of transition group IV of the Periodic Table of the Elements. Examples which may be mentioned here are enantioselective hydrogenations of prochiral substrates, for example prochiral olefins as described in R. Waymouth, P. Pino, J. Am. Chem. Soc. 112 (1990), pp. 4911–4914, or prochiral ketones, imines and oximes as described in WO 92/9545.

Mention may also be made of the preparation of optically active alkenes by enantioselective oligomerization, as described in W. Kaminsky et al., Angew. Chem. 101 (1989), pp. 1304–1306, and the enantioselective cyclopolymerization of 1,5-hexadienes as described in R. Waymouth, G. Coates, J. Am. Chem. Soc. 113 (1991), pp. 6270–6271.

The applications mentioned generally require the use of an ansa-metallocene complex in its racemic form, i.e. without meso compounds. In the case of the diastereomer mixture (rac. and meso form) obtained in the metallocene syntheses of the prior art, the meso form has to be separated off first. Since the meso form has to discarded, the yield of racemic ansa-metallocene complex is low.

EP-A 669340 describes a process for preparing bridged, stereorigid metallocene complexes using organotin halides. In this process, 2 mol of tin compound are required per mol of metallocene complex and the yield of metallocene complex is not yet satisfactory.

It is an object of the present invention to find a process for the selective preparation of racemic, virtually (NMR measurement accuracy) meso isomer-free ansa-metallocene complexes. A further object is to find tin compounds which can be reacted in a small amount, based on the transition metal halide, with a transition metal halide and thus give virtually meso-free racemic ansa-metallocene complexes.

We have found that this object is achieved by the process defined in the claims, the tin compounds II and a process for preparing the tin compounds II.

The terms "meso form", "racemate" and thus also "enantiomers" in the context of ansa-metallocene complexes are known and defined, for example, in Rheingold et al., Organometallics 11 (1992), pp. 1869–1876.

For the purposes of the present invention, the term "virtually meso-free" means that at least 90% of a compound is in the form of the racemate.

The racemic ansa-metallocene complexes which are obtained in the process of the present invention are those of the formula I

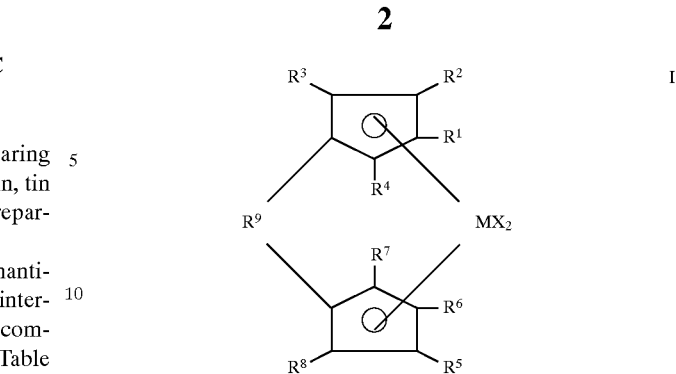

where the substituents and indices have the following meanings:

M is titanium, zirconium, hafnium, vanadium, niobium or tantalum,

X is fluorine, chlorine, bromine, iodine, hydrogen, $C_1$–$C_{10}$-alkyl, $C_6$–$C_{15}$-aryl or —$OR^{10}$, where $R^{10}$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical, $R^1$ to $R^8$ are hydrogen, $C_1$–$C_{10}$-alkyl, 5- to 7-membered cycloalkyl which may in turn bear a $C_1$–$C_{10}$-alkyl group as substituent, $C_6$–$C_{15}$-aryl or arylalkyl, where two adjacent radicals may also together form a cyclic group having from 4 to 14 carbon atoms, or $Si(R^{11})_3$ where $R^{11}$ is $C_1$–$C_{10}$-alkyl, $C_6$–$C_{15}$-aryl or $C_3$–$C_{10}$-cycloalkyl, $R^9$ is

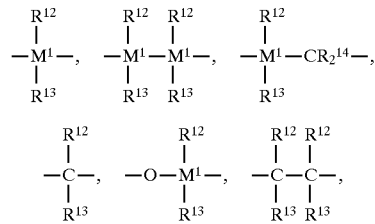

$=BR^{12}$, $=AlR^{12}$, —Ge—, —Sn—, —O—, —S—, $=SO$, $=SO_2$, $=NR^{12}$, $=CO$, $=PR^{12}$ or $=P(O)R^{12}$, where $R^{12}$, $R^{13}$ and $R^{14}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ or $R^{12}$ and $R^{14}$ in each case together with the atoms connecting them form a ring, and $M^1$ is silicon or germanium.

Particularly suitable ansa-metallocene complexes of the formula I are those in which M is titanium, zirconium or hafnium, X is chlorine or $C_1$–$C_6$-alkyl, $R^1$ to $R^8$ are hydrogen, $C_1$–$C_6$-alkyl, $C_1$–$C_{12}$-aryl or two adjacent radicals together form a cyclic group having from 4 to 15, in particular from 8 to 12, carbon atoms and $M^1$ is silicon.

Preference is given to ansa-metallocene complexes of the formula I, in their racemic form, which are substituted in the 2 position of both cyclopentadienyl rings, i.e. $R^4$ and $R^7$ in the formula I are different from hydrogen and are, in particular, methyl, ethyl, n-propyl, isopropyl, n-butyl, tert-butyl or phenyl.

Very particular preference is given to ansa-metallocene complexes of the formula I, in their racemic form, which are substituted in the 2 and 4 positions of the cyclopentadienyl rings, i.e. the substituents $R^4$ and $R^2$ and $R^7$ and $R^5$ in I are different from hydrogen and are, in particular, methyl, ethyl, n-propyl, isopropyl, n-butyl, tert-butyl or phenyl. The numbering of the ring positions of the cyclopentadienyl ligands is as shown in formula Ia.

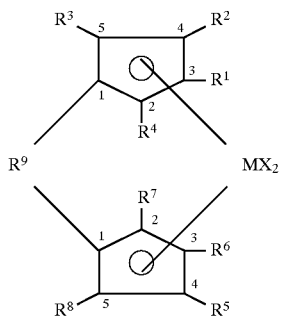

Furthermore, preference is given to those ansa-metallocene complexes which are silyl-bridged, i.e., in formula I,

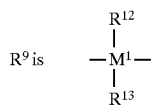

where $R^{12}$ and $R^{13}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_1$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ together with the atoms connecting them form a ring, and $M^1$ is silicon.

A particularly preferred bridging structure $R^9$ is dimethylsilyl.

Examples of particularly suitable ansa-metallocene complexes are:
dimethylsilanediylbis(2-methyl-4-methyl-1-cyclopentadienyl)zirconium dichloride
dimethylsilanediylbis(2-methyl-4-ethyl-1-cyclopentadienyl)zirconium dichloride
dimethylsilanediylbis(2-methyl-4-propyl-1-cyclopentadienyl)zirconium dichloride
dimethylsilanediylbis(2-methyl-4-butyl-1-cyclopentadienyl)zirconium dichloride
dimethylsilanediylbis(2-methyl-4-$^i$propyl-1-cyclopentadienyl)zirconium dichloride
dimethylsilanediylbis(2-methyl-4-$^i$butyl-1-cyclopentadienyl)zirconium dichloride
dimethylsilanediylbis(2-methyl-4-$^t$butyl-1-cyclopentadienyl)zirconium dichloride
dimethylsilanediylbis(2-methyl-4-trimethylsilyl-1-cyclopentadienyl)zirconium dichloride
dimethylsilanediylbis(2-methyl-4-phenyl-1-cyclopentadienyl)zirconium dichloride
dimethylsilanediylbis(2-ethyl-4-methyl-1-cyclopentadienyl)zirconium dichloride
dimethylsilanediylbis(2-ethyl-4-ethyl-1-cyclopentadienyl)zirconium dichloride
dimethylsilanediylbis(2-ethyl-4-propyl-1-cyclopentadienyl)zirconium dichloride
dimethylsilanediylbis(2-ethyl-4-butyl-1-cyclopentadienyl)zirconium dichloride
dimethylsilanediylbis(2-ethyl-4-$^i$propyl-1-cyclopentadienyl)zirconium dichloride
dimethylsilanediylbis(2-ethyl-4-$^i$butyl-1-cyclopentadienyl)zirconium dichloride
dimethylsilanediylbis(2-ethyl-4-$^t$butyl-1-cyclopentadienyl)zirconium dichloride
dimethylsilanediylbis(2-ethyl-4-trimethylsilyl-1-cyclopentadienyl)zirconium dichloride
dimethylsilanediylbis(2-ethyl-4-phenyl-1-cyclopentadienyl)zirconium dichloride
dimethylsilanediylbis(2-propyl-4-methyl-1-cyclopentadienyl)zirconium dichloride
dimethylsilanediylbis(2-propyl-4-ethyl-1-cyclopentadienyl)zirconium dichloride
dimethylsilanediylbis(2-propyl-4-propyl-1-cyclopentadienyl)zirconium dichloride
dimethylsilanediylbis(2-propyl-4-butyl-1-cyclopentadienyl)zirconium dichloride
dimethylsilanediylbis(2-propyl-4-$^i$propyl-1-cyclopentadienyl)zirconium dichloride
dimethylsilanediylbis(2-propyl-4-$^i$butyl-1-cyclopentadienyl)zirconium dichloride
dimethylsilanediylbis(2-propyl-4-$^t$butyl-1-cyclopentadienyl)zirconium dichloride
dimethylsilanediylbis(2-propyl-4-trimethylsilyl-1-cyclopentadienyl)zirconium dichloride
dimethylsilanediylbis(2-propyl-4-phenyl-1-cyclopentadienyl)zirconium dichloride
dimethylsilanediylbis(2-butyl-4-methyl-1-cyclopentadienyl)zirconium dichloride
dimethylsilanediylbis(2-butyl-4-ethyl-1-cyclopentadienyl)zirconium dichloride
dimethylsilanediylbis(2-butyl-4-propyl-1-cyclopentadienyl)zirconium dichloride
dimethylsilanediylbis(2-butyl-4-butyl-1-cyclopentadienyl)zirconium dichloride
dimethylsilanediylbis(2-butyl-4-$^i$propyl-1-cyclopentadienyl)zirconium dichloride
dimethylsilanediylbis(2-butyl-4-$^i$butyl-1-cyclopentadienyl)zirconium dichloride
dimethylsilanediylbis(2-butyl-4-$^t$butyl-1-cyclopentadienyl)zirconium dichloride
dimethylsilanediylbis(2-butyl-4-trimethylsilyl-1-cyclopentadienyl)zirconium dichloride
dimethylsilanediylbis(2-butyl-4-phenyl-1-cyclopentadienyl)zirconium dichloride
dimethylsilanediylbis(2-$^i$propyl-4-methyl1-cyclopentadienyl)zirconium dichloride
dimethylsilanediylbis(2-$^i$propyl-4-ethyl-1-cyclopentadienyl)zirconium dichloride
dimethylsilanediylbis(2-$^i$propyl-4-propyl-1-cyclopentadienyl)zirconium dichloride
dimethylsilanediylbis(2-$^i$propyl-4-butyl-1-cyclopentadienyl)zirconium dichloride
dimethylsilanediylbis(2-$^i$propyl-4-$^i$propyl-1-cyclopentadienyl)zirconium dichloride
dimethylsilanediylbis(2-$^i$propyl-4-$^i$butyl-1-cyclopentadienyl)zirconium dichloride
dimethylsilanediylbis(2-$^i$propyl-4-$^t$butyl-1-cyclopentadienyl)zirconium dichloride dimethylsilanediylbis(2-$^i$propyl-4-trimethylsilyl-1-cyclopentadienyl)zirconium dichloride
dimethylsilanediylbis(2-$^i$propyl-4-phenyl-1-cyclopentadienyl)zirconium dichloride
dimethylsilanediylbis(2-$^r$butyl-4-methyl-1-cyclopentadienyl)zirconium dichloride
dimethylsilanediylbis(2-$^r$butyl-4-ethyl-1-cyclopentadienyl)zirconium dichloride
dimethylsilanediylbis(2-$^r$butyl-4-propyl-1-cyclopentadienyl)zirconium dichloride
dimethylsilanediylbis(2-$^r$butyl-4-butyl-1-cyclopentadienyl)zirconium dichloride
dimethylsilanediylbis(2-$^r$butyl-4-$^i$propyl-1-cyclopentadienyl)zirconium dichloride
dimethylsilanediylbis(2-$^r$butyl-4-$^i$butyl-1-cyclopentadienyl)zirconium dichloride
dimethylsilanediylbis(2-$^r$butyl-4-$^r$butyl-1-cyclopentadienyl)zirconium dichloride
dimethylsilanediylbis(2-$^r$butyl-4-trimethylsilyl-1-cyclopentadienyl)zirconium dichloride
dimethylsilanediylbis(2-$^r$butyl-4-phenyl-1-cyclopentadienyl)zirconium dichloride
dimethylsilanediylbis(2-trimethylsilyl-4-methyl-1-cyclopentadienyl)zirconium dichloride
dimethylsilanediylbis(2-trimethylsilyl-4-ethyl-1-cyclopentadienyl)zirconium dichloride
dimethylsilanediylbis(2-trimethylsilyl-4-propyl-1-cyclopentadienyl)zirconium dichloride
dimethylsilanediylbis(2-trimethylsilyl-4-butyl-1-cyclopentadienyl)zirconium dichloride
dimethylsilanediylbis(2-trimethylsilyl-4-$^i$propyl-1-cyclopentadienyl)zirconium dichloride
dimethylsilanediylbis(2-trimethylsilyl-4-$^i$butyl-1-cyclopentadienyl)zirconium dichloride
dimethylsilanediylbis(2-trimethylsilyl-4-$^r$butyl-1-cyclopentadienyl)zirconium dichloride
dimethylsilanediylbis(2-trimethylsilyl-4-trimethylsilyl-1-cyclo-pentadienyl)zirconium dichloride
dimethylsilanediylbis(2-trimethylsilyl-4-phenyl-1-cyclopentadienyl)zirconium dichloride
dimethylsilanediylbis(2-phenyl-4-methyl-1-cyclopentadienyl)zirconium dichloride
dimethylsilanediylbis(2-phenyl-4-ethyl-1-cyclopentadienyl)zirconium dichloride
dimethylsilanediylbis(2-phenyl-4-propyl-1-cyclopentadienyl)zirconium dichloride
dimethylsilanediylbis(2-phenyl-4-butyl-1-cyclopentadienyl)zirconium dichloride
dimethylsilanediylbis(2-phenyl-4-$^i$propyl-1-cyclopentadienyl)zirconium dichloride
dimethylsilanediylbis(2-phenyl-4-$^i$butyl-1-cyclopentadienyl)zirconium dichloride
dimethylsilanediylbis(2-phenyl-4-$^r$butyl-1-cyclopentadienyl)zirconium dichloride
dimethylsilanediylbis(2-phenyl-4-trimethylsilyl-1-cyclopentadienyl)zirconium dichloride
dimethylsilanediylbis(2-phenyl-4-phenyl-1-cyclopentadienyl)zirconium dichloride
dimethylsilanediylbis(2-methyl-1-indenyl)zirconium dichloride
dimethylsilanediylbis(2-ethyl-1-indenyl)zirconium dichloride
dimethylsilanediylbis(2-propyl-1-indenyl)zirconium dichloride
dimethylsilanediylbis(2-butyl-1-indenyl)zirconium dichloride
dimethylsilanediylbis(2-$^i$propyl-1-indenyl)zirconium dichloride
dimethylsilanediylbis(2-$^r$butyl-1-indenyl)zirconium dichloride
dimethylsilanediylbis(2-trimethylsilyl-1-indenyl)zirconium dichloride
dimethylsilanediylbis(2-phenyl-1-indenyl)zirconium dichloride
dimethylsilanediylbis(2-methyl-4,5,6,7-tetrahydro-1-indenyl)zirconium dichloride
dimethylsilanediylbis(2-ethyl-4,5,6,7-tetrahydro-1-indenyl)zirconium dichloride
dimethylsilanediylbis(2-propyl-4,5,6,7-tetrahydro-1-indenyl)zirconium dichloride
dimethylsilanediylbis(2-butyl-4,5,6,7-tetrahydro-1-indenyl)zirconium dichloride
dimethylsilanediylbis(2-$^i$propyl-4,5,6,7-tetrahydro-1-indenyl)zirconium dichloride
dimethylsilanediylbis(2-$^r$butyl-4,5,6,7-tetrahydro-1-indenyl)zirconium dichloride
dimethylsilanediylbis(2-trimethylsilyl-4,5,6,7-tetrahydro-1-indenyl)zirconium dichloride
dimethylsilanediylbis(2-phenyl-4,5,6,7-tetrahydro-1-indenyl)zirconium dichloride
dimethylsilanediylbis(2-methyl-4,7-dimethyl-1-indenyl)zirconium dichloride
dimethylsilanediylbis(2-ethyl-4,7-dimethyl-1-indenyl)zirconium dichloride
dimethylsilanediylbis(2-propyl-4,7-dimethyl-1-indenyl)zirconium dichloride
dimethylsilanediylbis(2-butyl-4,7-dimethyl-1-indenyl)zirconium dichloride
dimethylsilanediylbis(2-$^i$propyl-4,7-dimethyl-1-indenyl)zirconium dichloride
dimethylsilanediylbis(2-$^r$butyl-4,7-dimethyl-1-indenyl)zirconium dichloride
dimethylsilanediylbis(2-trimethylsilyl-4,7-dimethyl-1-indenyl)zirconium dichloride
dimethylsilanediylbis(2-phenyl-4,7-dimethyl-1-indenyl)zirconium dichloride
dimethylsilanediylbis(2-methyl-4,6-di-$^i$propyl-1-indenyl)zirconium dichloride
dimethylsilanediylbis(2-ethyl-4,6-di-$^i$propyl-1-indenyl)zirconium dichloride
dimethylsilanediylbis(2-propyl-4,6-di-$^i$propyl-1-indenyl)zirconium dichloride
dimethylsilanediylbis(2-butyl-4,6-di-$^i$propyl-1-indenyl)zirconium dichloride
dimethylsilanediylbis(2-$^i$propyl-4,6-di-$^i$propyl-1-indenyl)zirconium dichloride
dimethylsilanediylbis(2-$^r$butyl-4,6-di-$^i$propyl-1-indenyl)zirconium dichloride
dimethylsilanediylbis(2-trimethylsilyl-4,6-di-$^i$propyl-1-indenyl)zirconium dichloride
dimethylsilanediylbis(2-phenyl-4,6-di-$^i$propyl-1-indenyl)zirconium dichloride
dimethylsilanediylbis(2-methyl-1-benzindenyl)zirconium dichloride
dimethylsilanediylbis(2-ethyl-1-benzindenyl)zirconium dichloride
dimethylsilanediylbis(2-propyl-1-benzindenyl)zirconium dichloride
dimethylsilanediylbis(2-butyl-1-benzindenyl)zirconium dichloride
dimethylsilanediylbis(2-$^i$propyl-1-benzindenyl)zirconium dichloride
dimethylsilanediylbis(2-$^r$butyl-1-benzindenyl)zirconium dichloride
dimethylsilanediylbis(2-trimethylsilyl-1-benzindenyl)zirconium dichloride dimethylsilanediylbis(2-phenyl-1-benzindenyl)zirconium dichloride
dimethylsilanediylbis(2-methyl-4-phenyl-1-indenyl)zirconium dichloride
dimethylsilanediylbis(2-ethyl-4-phenyl-1-indenyl)zirconium dichloride
dimethylsilanediylbis(2-propyl-4-phenyl-1-indenyl)zirconium dichloride
dimethylsilanediylbis(2-butyl-4-phenyl-1-indenyl)zirconium dichloride
dimethylsilanediylbis(2-$^i$propyl-4-phenyl-1-indenyl)zirconium dichloride
dimethylsilanediylbis(2-$^t$butyl-4-phenyl-1-indenyl)zirconium dichloride
dimethylsilanediylbis(2-trimethylsilyl-4-phenyl-1-indenyl)zirconium dichloride
dimethylsilanediylbis(2-phenyl-4-phenyl-1-indenyl)zirconium dichloride
dimethylsilanediylbis(2-methyl-4-naphthyl-1-indenyl)zirconium dichloride
dimethylsilanediylbis(2-ethyl-4-naphthyl-1-indenyl)zirconium dichloride
dimethylsilanediylbis(2-propyl-4-naphthyl-1-indenyl)zirconium dichloride
dimethylsilanediylbis(2-butyl-4-naphthyl-1-indenyl)zirconium dichloride
dimethylsilanediylbis(2-$^i$propyl-4-naphthyl-1-indenyl)zirconium dichloride
dimethylsilanediylbis(2-$^t$butyl-4-naphthyl-1-indenyl)zirconium dichloride
dimethylsilanediylbis(2-trimethylsilyl-4-naphthyl-1-indenyl)zirconium dichloride
dimethylsilanediylbis(2-phenyl-4-naphthyl-1-indenyl)zirconium dichloride
dimethylsilanediylbis(2-methyl-4-methyl-1-cyclopentadienyl)titanium dichloride
dimethylsilanediylbis(2-methyl-4-ethyl-1-cyclopentadienyl)titanium dichloride
dimethylsilanediylbis(2-methyl-4-propyl-1-cyclopentadienyl)titanium dichloride
dimethylsilanediylbis(2-methyl-4-butyl-1-cyclopentadienyl)titanium dichloride
dimethylsilanediylbis(2-methyl-4-$^i$propyl-1-cyclopentadienyl)titanium dichloride
dimethylsilanediylbis(2-methyl-4-$^i$butyl-1-cyclopentadienyl)titanium dichloride
dimethylsilanediylbis(2-methyl-4-$^t$butyl-1-cyclopentadienyl)titanium dichloride
dimethylsilanediylbis(2-methyl-4-trimethylsilyl-1-cyclopentadienyl)titanium dichloride
dimethylsilanediylbis(2-methyl-4-phenyl-1-cyclopentadienyl)titanium dichloride
dimethylsilanediylbis(2-ethyl-4-methyl-1-cyclopentadienyl)titanium dichloride
dimethylsilanediylbis(2-ethyl-4-ethyl-1-cyclopentadienyl)titanium dichloride
dimethylsilanediylbis(2-ethyl-4-propyl-1-cyclopentadienyl)titanium dichloride
dimethylsilanediylbis(2-ethyl-4-butyl-1-cyclopentadienyl)titanium dichloride
dimethylsilanediylbis (2-ethyl-4-$^i$propyl-1-cyclopentadienyl)titanium dichloride
dimethylsilanediylbis(2-ethyl-4-$^i$butyl-1-cyclopentadienyl)titanium dichloride
dimethylsilanediylbis(2-ethyl-4-$^t$butyl-1-cyclopentadienyl)titanium dichloride
dimethylsilanediylbis(2-ethyl-4-trimethylsilyl-1-cyclopentadienyl)titanium dichloride
dimethylsilanediylbis(2-ethyl-4-phenyl-1-cyclopentadienyl)titanium dichloride
dimethylsilanediylbis(2-propyl-4-methyl-1-cyclopentadienyl)titanium dichloride
dimethylsilanediylbis(2-propyl-4-ethyl-1-cyclopentadienyl)titanium dichloride
dimethylsilanediylbis(2-propyl-4-propyl-1-cyclopentadienyl)titanium dichloride
dimethylsilanediylbis(2-propyl-4-butyl-1-cyclopentadienyl)titanium dichloride
dimethylsilanediylbis(2-propyl-4-$^i$propyl-1-cyclopentadienyl)titanium dichloride
dimethylsilanediylbis(2-propyl-4-$^i$butyl-1-cyclopentadienyl)titanium dichloride
dimethylsilanediylbis(2-propyl-4-$^t$butyl-1-cyclopentadienyl)titanium dichloride
dimethylsilanediylbis(2-propyl-4-trimethylsilyl-1-cyclopentadienyl)titanium dichloride
dimethylsilanediylbis(2-propyl-4-phenyl-1-cyclopentadienyl)titanium dichloride
dimethylsilanediylbis(2-butyl-4-methyl-1-cyclopentadienyl)titanium dichloride
dimethylsilanediylbis(2-butyl-4-ethyl-1-cyclopentadienyl)titanium dichloride
dimethylsilanediylbis(2-butyl-4-propyl-1-cyclopentadienyl)titanium dichloride
dimethylsilanediylbis(2-butyl-4-butyl-1-cyclopentadienyl)titanium dichloride
dimethylsilanediylbis(2-butyl-4-$^i$propyl-1-cyclopentadienyl)titanium dichloride
dimethylsilanediylbis(2-butyl-4-$^i$butyl-1-cyclopentadienyl)titanium dichloride
dimethylsilanediylbis(2-butyl-4-trimethylsilyl-1-cyclopentadienyl)titanium dichloride
dimethylsilanediylbis(2-butyl-4-phenyl-1-cyclopentadienyl)titanium dichloride
dimethylsilanediylbis(2-$^i$propyl-4-methyl-1-cyclopentadienyl)titanium dichloride
dimethylsilanediylbis(2-$^i$propyl-4-ethyl-1-cyclopentadienyl)titanium dichloride
dimethylsilanediylbis(2-$^i$propyl-4-propyl-1-cyclopentadienyl)titanium dichloride
dimethylsilanediylbis(2-$^i$propyl-4-butyl-1-cyclopentadienyl)titanium dichloride
dimethylsilanediylbis(2-$^i$propyl-4-$^i$propyl-1-cyclopentadienyl)titanium dichloride
dimethylsilanediylbis(2-$^i$propyl-4-$^i$butyl-1-cyclopentadienyl)titanium dichloride
dimethylsilanediylbis(2-$^i$propyl-4-$^t$butyl-1-cyclopentadienyl)titanium dichloride
dimethylsilanediylbis(2-$^i$propyl-4-trimethylsilyl-1-cyclopentadienyl)titanium dichloride
dimethylsilanediylbis(2-$^i$propyl-4-phenyl-1-cyclopentadienyl)titanium dichloride
dimethylsilanediylbis(2-$^t$butyl-4-methyl-1-cyclopentadienyl)titanium dichloride
dimethylsilanediylbis(2-$^t$butyl-4-ethyl-1-cyclopentadienyl)titanium dichloride
dimethylsilanediylbis(2-$^t$butyl-4-propyl-1-cyclopentadienyl)titanium dichloride
dimethylsilanediylbis(2-$^t$butyl-4-butyl-1-cyclopentadienyl)titanium dichloride
dimethylsilanediylbis(2-$^t$butyl-4-$^i$propyl-1-cyclopentadienyl)titanium dichloride
dimethylsilanediylbis(2-$^t$butyl-4-$^i$butyl-1-cyclopentadienyl)titanium dichloride
dimethylsilanediylbis(2-$^t$butyl-4-$^t$butyl-1-cyclopentadienyl)titanium dichloride dimethylsilanediylbis(2-$^t$butyl-4-trimethylsilyl-1-cyclopentadienyl)titanium dichloride
dimethylsilanediylbis(2-$^t$butyl-4-phenyl-1-cyclopentadienyl)titanium dichloride
dimethylsilanediylbis(2-trimethylsilyl-4-methyl-1-cyclopentadienyl)titanium dichloride
dimethylsilanediylbis(2-trimethylsilyl-4-ethyl-1-cyclopentadienyl)titanium dichloride
dimethylsilanediylbis(2-trimethylsilyl-4-propyl-1-cyclopentadienyl)titanium dichloride
dimethylsilanediylbis(2-trimethylsilyl-4-butyl-1-cyclopentadienyl)titanium dichloride
dimethylsilanediylbis(2-trimethylsilyl-4-$^i$propyl-1-cyclopentadienyl)titanium dichloride
dimethylsilanediylbis(2-trimethylsilyl-4-$^i$butyl-1-cyclopentadienyl)titanium dichloride
dimethylsilanediylbis(2-trimethylsilyl-4-$^t$butyl-1-cyclopentadienyl)titanium dichloride
dimethylsilanediylbis(2-trimethylsilyl-4-trimethylsilyl-1-cyclo-pentadienyl)titanium dichloride
dimethylsilanediylbis(2-trimethylsilyl-4-phenyl-1-cyclopentadienyl)titanium dichloride
dimethylsilanediylbis(2-phenyl-4-methyl-1-cyclopentadienyl)titanium dichloride
dimethylsilanediylbis(2-phenyl-4-ethyl-1-cyclopentadienyl)titanium dichloride
dimethylsilanediylbis(2-phenyl-4-propyl-1-cyclopentadienyl)titanium dichloride
dimethylsilanediylbis(2-phenyl-4-butyl-1-cyclopentadienyl)titanium dichloride
dimethylsilanediylbis(2-phenyl-4-$^i$butyl-1-cyclopentadienyl)titanium dichloride
dimethylsilanediylbis(2-phenyl-4-$^t$butyl-1-cyclopentadienyl)titanium dichloride
dimethylsilanediylbis(2-phenyl-4-trimethylsilyl-1-cyclopentadienyl)titanium dichloride
dimethylsilanediylbis(2-phenyl-4-phenyl-1-cyclopentadienyl)titanium dichloride
dimethylsilanediylbis(2-methyl-1-indenyl)titanium dichloride
dimethylsilanediylbis(2-ethyl-1-indenyl)titanium dichloride
dimethylsilanediylbis(2-propyl-1-indenyl)titanium dichloride
dimethylsilanediylbis(2-butyl-1-indenyl)titanium dichloride
dimethylsilanediylbis(2-$^i$propyl-1-indenyl)titanium dichloride
dimethylsilanediylbis(2-$^t$butyl-1-indenyl)titanium dichloride
dimethylsilanediylbis(2-trimethylsilyl-1-indenyl)titanium dichloride
dimethylsilanediylbis(2-phenyl-1-indenyl)titanium dichloride
dimethylsilanediylbis(2-methyl-4,5,6,7-tetrahydro-1-indenyl)titanium dichloride
dimethylsilanediylbis(2-ethyl-4,5,6,7-tetrahydro-1-indenyl)titanium dichloride
dimethylsilanediylbis(2-propyl-4,5,6,7-tetrahydro-1-indenyl)titanium dichloride
dimethylsilanediylbis(2-butyl-4,5,6,7-tetrahydro-1-indenyl)titanium dichloride
dimethylsilanediylbis(2-$^i$propyl-4,5,6,7-tetrahydro-1-indenyl)titanium dichloride
dimethylsilanediylbis(2-$^t$butyl-4,5,6,7-tetrahydro-1-indenyl)titanium dichloride
dimethylsilanediylbis(2-trimethylsilyl-4,5,6,7-tetrahydro-1-indenyl)titanium dichloride
dimethylsilanediylbis(2-phenyl-4,5,6,7-tetrahydro-1-indenyl)titanium dichloride
dimethylsilanediylbis(2-methyl-4,7-dimethyl-1-indenyl)titanium dichloride
dimethylsilanediylbis(2-ethyl-4,7-dimethyl-1-indenyl)titanium dichloride
dimethylsilanediylbis(2-propyl-4,7-dimethyl-1-indenyl)titanium dichloride
dimethylsilanediylbis(2-butyl-4,7-dimethyl-1-indenyl)titanium dichloride
dimethylsilanediylbis(2-$^i$propyl-4,7-dimethyl-1-indenyl)titanium dichloride
dimethylsilanediylbis(2-$^t$butyl-4,7-dimethyl-1-indenyl)titanium dichloride
dimethylsilanediylbis(2-trimethylsilyl-4,7-dimethyl-1-indenyl)titanium dichloride
dimethylsilanediylbis(2-phenyl-4,7-dimethyl-1-indenyl)titanium dichloride
dimethylsilanediylbis(2-methyl-4,6-di-$^i$propyl-1-indenyl)titanium dichloride
dimethylsilanediylbis(2-ethyl-4,6-di-$^i$propyl-1-indenyl)titanium dichloride
dimethylsilanediylbis(2-propyl-4,6-di-$^i$propyl-1-indenyl)titanium dichloride
dimethylsilanediylbis(2-butyl-4,6-di-$^i$propyl-1-indenyl)titanium dichloride
dimethylsilanediylbis(2-$^i$propyl-4,6-di-$^i$propyl-1-indenyl)titanium dichloride
dimethylsilanediylbis(2-$^t$butyl-4,6-di-$^i$propyl-1-indenyl)titanium dichloride
dimethylsilanediylbis(2-trimethylsilyl-4,6-di-$^i$propyl-1-indenyl)titanium dichloride
dimethylsilanediylbis(2-phenyl-4,6-di-$^i$propyl-1-indenyl)titanium dichloride
dimethylsilanediylbis(2-methyl-1-benzindenyl)titanium dichloride
dimethylsilanediylbis(2-ethyl-1-benzindenyl)titanium dichloride
dimethylsilanediylbis(2-propyl-1-benzindenyl)titanium dichloride
dimethylsilanediylbis(2-butyl-1-benzindenyl)titanium dichloride
dimethylsilanediylbis(2-$^i$propyl-1-benzindenyl)titanium dichloride
dimethylsilanediylbis(2-$^t$butyl-1-benzindenyl)titanium dichloride
dimethylsilanediylbis(2-trimethylsilyl-1-benzindenyl)titanium dichloride
dimethylsilanediylbis(2-phenyl-1-benzindenyl)titanium dichloride
dimethylsilanediylbis(2-methyl-4-phenyl-1-indenyl)titanium dichloride
dimethylsilanediylbis(2-ethyl-4-phenyl-1-indenyl)titanium dichloride
dimethylsilanediylbis(2-propyl-4-phenyl-1-indenyl)titanium dichloride
dimethylsilanediylbis(2-butyl-4-phenyl-1-indenyl)titanium dichloride
dimethylsilanediylbis(2-$^i$propyl-4-phenyl-1-indenyl)titanium dichloride
dimethylsilanediylbis(2-$^t$butyl-4-phenyl-1-indenyl)titanium dichloride
dimethylsilanediylbis(2-trimethylsilyl-4-phenyl-1-indenyl)titanium dichloride
dimethylsilanediylbis(2-phenyl-4-phenyl-1-indenyl)titanium dichloride
dimethylsilanediylbis(2-methyl-4-naphthyl-1-indenyl)titanium dichloride
dimethylsilanediylbis(2-ethyl-4-naphthyl-1-indenyl)titanium dichloride dimethylsilanediylbis(2-propyl-4-naphthyl-1-indenyl) titanium dichloride
dimethylsilanediylbis(2-butyl-4-naphthyl-1-indenyl) titanium dichloride
dimethylsilanediylbis(2-$^i$propyl-4-naphthyl-1-indenyl) titanium dichloride
dimethylsilanediylbis(2-$^t$butyl-4-naphthyl-1-indenyl) titanium dichloride
dimethylsilanediylbis(2-trimethylsilyl-4-naphthyl-1-indenyl)titanium dichloride
dimethylsilanediylbis(2-phenyl-4-naphthyl-1-indenyl) titanium dichloride
dimethylsilanediylbis(2-methyl-4-methyl-1-cyclopentadienyl)hafnium dichloride
dimethylsilanediylbis(2-methyl-4-ethyl-1-cyclopentadienyl)hafnium dichloride
dimethylsilanediylbis(2-methyl-4-propyl-1-cyclopentadienyl)hafnium dichloride
dimethylsilanediylbis(2-methyl-4-butyl-1-cyclopentadienyl)hafnium dichloride
dimethylsilanediylbis(2-methyl-4-$^i$propyl-1-cyclopentadienyl)hafnium dichloride
dimethylsilanediylbis(2-methyl-4-$^i$butyl-1-cyclopentadienyl)hafnium dichloride
dimethylsilanediylbis(2-methyl-4-$^t$butyl-1-cyclopentadienyl)hafnium dichloride
dimethylsilanediylbis(2-methyl-4-trimethylsilyl-1-cyclopentadienyl)hafnium dichloride
dimethylsilanediylbis(2-methyl-4-phenyl-1-cyclopentadienyl)hafnium dichloride
dimethylsilanediylbis(2-ethyl-4-methyl-1-cyclopentadienyl)hafnium dichloride
dimethylsilanediylbis(2-ethyl-4-ethyl-1-cyclopentadienyl) hafnium dichloride
dimethylsilanediylbis(2-ethyl-4-propyl-1-cyclopentadienyl) hafnium dichloride
dimethylsilanediylbis(2-ethyl-4-butyl-1-cyclopentadienyl) hafnium dichloride
dimethylsilanediylbis(2-ethyl-4-$^i$propyl-1-cyclopentadienyl)hafnium dichloride
dimethylsilanediylbis(2-ethyl-4-butyl-1-cyclopentadienyl) hafnium dichloride
dimethylsilanediylbis(2-ethyl-4-$^t$butyl-1-cyclopentadienyl) hafnium dichloride
dimethylsilanediylbis(2-ethyl-4-trimethylsilyl-1-cyclopentadienyl)hafnium dichloride
dimethylsilanediylbis(2-ethyl-4-phenyl-1-cyclopentadienyl) hafnium dichloride
dimethylsilanediylbis(2-propyl-4-methyl-1-cyclopentadienyl)hafnium dichloride
dimethylsilanediylbis(2-propyl-4-ethyl-1-cyclopentadienyl) hafnium dichloride
dimethylsilanediylbis(2-propyl-4-propyl-1-cyclopentadienyl)hafnium dichloride
dimethylsilanediylbis(2-propyl-4-butyl-1-cyclopentadienyl) hafnium dichloride
dimethylsilanediylbis(2-propyl-4-$^i$propyl-1-cyclopentadienyl)hafnium dichloride
dimethylsilanediylbis(2-propyl-4-$^i$butyl-1-cyclopentadienyl)hafnium dichloride
dimethylsilanediylbis(2-propyl-4-$^t$butyl-1-cyclopentadienyl)hafnium dichloride
dimethylsilanediylbis(2-propyl-4-trimethylsilyl-1-cyclopentadienyl)hafnium dichloride
dimethylsilanediylbis(2-propyl-4-phenyl-1-cyclopentadienyl)hafnium dichloride
dimethylsilanediylbis(2-butyl-4-methyl-1-cyclopentadienyl)hafnium dichloride
dimethylsilanediylbis(2-butyl-4-ethyl-1-cyclopentadienyl) hafnium dichloride
dimethylsilanediylbis(2-butyl-4-propyl-1-cyclopentadienyl) hafnium dichloride
dimethylsilanediylbis(2-butyl-4-butyl-1-cyclopentadienyl) hafnium dichloride
dimethylsilanediylbis(2-butyl-4-$^i$propyl-1-cyclopentadienyl)hafnium dichloride
dimethylsilanediylbis(2-butyl-4-$^i$butyl-1-cyclopentadienyl) hafnium dichloride
dimethylsilanediylbis(2-butyl-4-$^t$butyl-1-cyclopentadienyl) hafnium dichloride
dimethylsilanediylbis(2-butyl-4-trimethylsilyl-1-cyclopentadienyl)hafnium dichloride
dimethylsilanediylbis(2-butyl-4-phenyl-1-cyclopentadienyl)hafnium dichloride
dimethylsilanediylbis(2-$^i$propyl-4-methyl-1-cyclopentadienyl)hafnium dichloride
dimethylsilanediylbis(2-$^i$propyl-4-ethyl-1-cyclopentadienyl)hafnium dichloride
dimethylsilanediylbis(2-$^i$propyl-4-propyl-1-cyclopentadienyl)hafnium dichloride
dimethylsilanediylbis(2-$^i$propyl-4-butyl-1-cyclopentadienyl)hafnium dichloride
dimethylsilanediylbis(2-$^i$propyl-4-$^i$propyl-1-cyclopentadienyl)hafnium dichloride
dimethylsilanediylbis(2-$^i$propyl-4-$^i$butyl-1-cyclopentadienyl)hafnium dichloride
dimethylsilanediylbis(2-$^i$propyl-4-$^t$butyl-1-cyclopentadienyl)hafnium dichloride
dimethylsilanediylbis(2-$^i$propyl-4-trimethylsilyl-1-cyclopentadienyl)hafnium dichloride
dimethylsilanediylbis(2-$^i$propyl-4-phenyl-1-cyclopentadienyl)hafnium dichloride
dimethylsilanediylbis(2-$^t$butyl-4-methyl-1-cyclopentadienyl)hafnium dichloride
dimethylsilanediylbis(2-$^t$butyl-4-ethyl-1-cyclopentadienyl) hafnium dichloride
dimethylsilanediylbis(2-$^t$butyl-4-propyl-1-cyclopentadienyl)hafnium dichloride
dimethylsilanediylbis(2-$^t$butyl-4-butyl-1-cyclopentadienyl) hafnium dichloride
dimethylsilanediylbis(2-$^t$butyl-4-$^i$propyl-1-cyclopentadienyl)hafnium dichloride
dimethylsilanediylbis(2-$^t$butyl-4-$^i$butyl-1-cyclopentadienyl) hafnium dichloride
dimethylsilanediylbis(2-$^t$butyl-4-$^t$butyl-1-cyclopentadienyl) hafnium dichloride
dimethylsilanediylbis(2-$^t$butyl-4-trimethylsilyl-1-cyclopentadienyl)hafnium dichloride
dimethylsilanediylbis(2-$^t$butyl-4-phenyl-1-cyclopentadienyl)hafnium dichloride
dimethylsilanediylbis(2-trimethylsilyl-4-methyl-1-cyclopentadienyl)hafnium dichloride
dimethylsilanediylbis(2-trimethylsilyl-4-ethyl-1-cyclopentadienyl)hafnium dichloride
dimethylsilanediylbis(2-trimethylsilyl-4-propyl-1-cyclopentadienyl)hafnium dichloride
dimethylsilanediylbis(2-trimethylsilyl-4-butyl-1-cyclopentadienyl)hafnium dichloride
dimethylsilanediylbis(2-trimethylsilyl-4-$^i$propyl-1-cyclopentadienyl)hafnium dichloride
dimethylsilanediylbis(2-trimethylsilyl-4-$^i$butyl-1-cyclopentadienyl)hafnium dichloride
dimethylsilanediylbis(2-trimethylsilyl-4-$^t$butyl-1-cyclopentadienyl)hafnium dichloride
dimethylsilanediylbis(2-trimethylsilyl-4-trimethylsilyl-1-cyclo-pentadienyl)hafnium dichloride dimethylsilanediylbis(2-trimethylsilyl-4-phenyl-1-cyclopentadienyl)hafnium dichloride
dimethylsilanediylbis(2-phenyl-4-methyl-1-cyclopentadienyl)hafnium dichloride
dimethylsilanediylbis(2-phenyl-4-ethyl-1-cyclopentadienyl)hafnium dichloride
dimethylsilanediylbis(2-phenyl-4-propyl-1-cyclopentadienyl)hafnium dichloride
dimethylsilanediylbis(2-phenyl-4-butyl-1-cyclopentadienyl)hafnium dichloride
dimethylsilanediylbis(2-phenyl-4-$^i$propyl-1-cyclopentadienyl)hafnium dichloride
dimethylsilanediylbis(2-phenyl-4-$^i$butyl-1-cyclopentadienyl)hafnium dichloride
dimethylsilanediylbis(2-phenyl-4-$^t$butyl-1-cyclopentadienyl)hafnium dichloride
dimethylsilanediylbis(2-phenyl-4-trimethylsilyl-1-cyclopentadienyl)hafnium dichloride
dimethylsilanediylbis(2-phenyl-4-phenyl-1-cyclopentadienyl)hafnium dichloride
dimethylsilanediylbis(2-methyl-1-indenyl)hafnium dichloride
dimethylsilanediylbis(2-ethyl-1-indenyl)hafnium dichloride
dimethylsilanediylbis(2-propyl-1-indenyl)hafnium dichloride
dimethylsilanediylbis(2-butyl-1-indenyl)hafnium dichloride
dimethylsilanediylbis(2-$^i$propyl-1-indenyl)hafnium dichloride
dimethylsilanediylbis(2-$^t$butyl-1-indenyl)hafnium dichloride
dimethylsilanediylbis(2-trimethylsilyl-1-indenyl)hafnium dichloride
dimethylsilanediylbis(2-phenyl-1-indenyl)hafnium dichloride
dimethylsilanediylbis(2-methyl-4,5,6,7-tetrahydro-1-indenyl)hafnium dichloride
dimethylsilanediylbis(2-ethyl-4,5,6,7-tetrahydro-1-indenyl)hafnium dichloride
dimethylsilanediylbis(2-propyl-4,5,6,7-tetrahydro-1-indenyl)hafnium dichloride
dimethylsilanediylbis(2-butyl-4,5,6,7-tetrahydro-1-indenyl)hafnium dichloride
dimethylsilanediylbis(2-$^i$propyl-4,5,6,7-tetrahydro-1-indenyl)hafnium dichloride
dimethylsilanediylbis(2-$^t$butyl-4,5,6,7-tetrahydro-1-indenyl)hafnium dichloride
dimethylsilanediylbis(2-trimethylsilyl-4,5,6,7-tetrahydro-1-indenyl)hafnium dichloride
dimethylsilanediylbis(2-phenyl-4,5,6,7-tetrahydro-1-indenyl)hafnium dichloride
dimethylsilanediylbis(2-methyl-4,7-dimethyl-1-indenyl)hafnium dichloride
dimethylsilanediylbis(2-ethyl-4,7-dimethyl-1-indenyl)hafnium dichloride
dimethylsilanediylbis(2-propyl-4,7-dimethyl-1-indenyl)hafnium dichloride
dimethylsilanediylbis(2-butyl-4,7-dimethyl-1-indenyl)hafnium dichloride
dimethylsilanediylbis(2-$^i$propyl-4,7-dimethyl-1-indenyl)hafnium dichloride
dimethylsilanediylbis(2-$^t$butyl-4,7-dimethyl-1-indenyl)hafnium dichloride
dimethylsilanediylbis(2-trimethylsilyl-4,7-dimethyl-1-indenyl)hafnium dichloride
dimethylsilanediylbis(2-phenyl-4,7-dimethyl-1-indenyl)hafnium dichloride
dimethylsilanediylbis(2-methyl-4,6-di-$^i$propyl-1-indenyl)hafnium dichloride
dimethylsilanediylbis(2-ethyl-4,6-di-$^i$propyl-1-indenyl)hafnium dichloride
dimethylsilanediylbis(2-propyl-4,6-di-$^i$propyl-1-indenyl)hafnium dichloride
dimethylsilanediylbis(2-butyl-4,6-di-$^i$propyl-1-indenyl)hafnium dichloride
dimethylsilanediylbis(2-$^i$propyl-4,6-di-$^i$propyl-1-indenyl)hafnium dichloride
dimethylsilanediylbis(2-$^t$butyl-4,6-di-$^i$propyl-1-indenyl)hafnium dichloride
dimethylsilanediylbis(2-trimethylsilyl-4,6-di-$^i$propyl-1-indenyl)hafnium dichloride
dimethylsilanediylbis(2-phenyl-4,6-di-$^i$propyl-1-indenyl)hafnium dichloride
dimethylsilanediylbis(2-methyl-1-benzindenyl)hafnium dichloride
dimethylsilanediylbis(2-ethyl-1-benzindenyl)hafnium dichloride
dimethylsilanediylbis(2-propyl-1-benzindenyl)hafnium dichloride
dimethylsilanediylbis(2-butyl-1-benzindenyl)hafnium dichloride
dimethylsilanediylbis(2-$^i$propyl-1-benzindenyl)hafnium dichloride
dimethylsilanediylbis(2-$^t$butyl-1-benzindenyl)hafnium dichloride
dimethylsilanediylbis(2-trimethylsilyl-1-benzindenyl)hafnium dichloride
dimethylsilanediylbis(2-phenyl-1-benzindenyl)hafnium dichloride
dimethylsilanediylbis(2-methyl-4-phenyl-1-indenyl)hafnium dichloride
dimethylsilanediylbis(2-ethyl-4-phenyl-1-indenyl)hafnium dichloride
dimethylsilanediylbis(2-propyl-4-phenyl-1-indenyl)hafnium dichloride
dimethylsilanediylbis(2-butyl-4-phenyl-1-indenyl)hafnium dichloride
dimethylsilanediylbis(2-$^i$propyl-4-phenyl-1-indenyl)hafnium dichloride
dimethylsilanediylbis(2-$^t$butyl-4-phenyl-1-indenyl)hafnium dichloride
dimethylsilanediylbis(2-trimethylsilyl-4-phenyl-1-indenyl)hafnium dichloride
dimethylsilanediylbis(2-phenyl-4-phenyl-1-indenyl)hafnium dichloride
dimethylsilanediylbis(2-methyl-4-naphthyl-1-indenyl)hafnium dichloride
dimethylsilanediylbis(2-ethyl-4-naphthyl-1-indenyl)hafnium dichloride
dimethylsilanediylbis(2-propyl-4-naphthyl-1-indenyl)hafnium dichloride
dimethylsilanediylbis(2-butyl-4-naphthyl-1-indenyl)hafnium dichloride
dimethylsilanediylbis(2-$^i$propyl-4-naphthyl-1-indenyl)hafnium dichloride
dimethylsilanediylbis(2-$^t$butyl-4-naphthyl-1-indenyl)hafnium dichloride
dimethylsilanediylbis(2-trimethylsilyl-4-naphthyl-1-indenyl)hafnium dichloride
dimethylsilanediylbis(2-phenyl-4-naphthyl-1-indenyl)hafnium dichloride
and also the analogous diphenylsilylene-bridged complexes.

The tin compounds of the present invention are those of the formula II

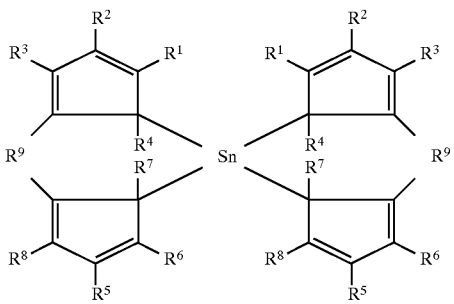

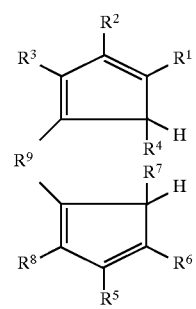

where

R$^1$ to R$^8$ are hydrogen, C$_1$–C$_{10}$-alkyl, 5- to 7-membered cycloalkyl which may in turn bear a C$_1$–C$_{10}$-alkyl group as substituent, C$_6$–C$_{15}$-aryl or arylalkyl, where two adjacent radicals may also together form a cyclic group having from 4 to 15 carbon atoms, or Si(R$^{11}$)$_3$ where R$^{11}$ is C$_1$–C$_{10}$-alkyl, C$_6$–C$_{15}$-aryl or C$_3$–C$_{10}$-cycloalkyl, R$^9$ is

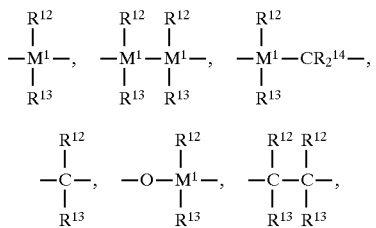

=BR$^{12}$, =AlR$^{12}$, —Ge—, —O—, —S—, =SO, =SO$_2$, =NR$^{12}$, =CO, =PR$^{12}$ or =P(O)R$^{12}$, where R$^{12}$, R$^{13}$ and R$^{14}$ are identical or different and are each a hydrogen atom, a halogen atom, a C$_1$–C$_{10}$-alkyl group, a C$_1$–C$_{10}$-fluoroalkyl group, a C$_6$–C$_{10}$-fluoroaryl group, a C$_6$–C$_{10}$-aryl group, a C$_1$–C$_{10}$-alkoxy group, a C$_2$–C$_{10}$-alkenyl group, a C$_7$–C$_{40}$-arylalkyl group, a C$_8$–C$_{40}$-arylalkenyl group or a C$_7$–C$_{40}$-alkylaryl group or R$^{12}$ and R$^{13}$ or R$^{12}$ and R$^{14}$ in each case together with the atoms connecting them form a ring, and M$^1$ is silicon or germanium.

Preferably, the tin compounds II are in racemic form. Particular preference is given those tin compounds II in which the identical or different substituents R$^2$, R$^5$ are C$_1$–C$_{10}$-alkyl, 5- to 7-membered cycloalkyl which may in turn bear a C$_1$–C$_{10}$-alkyl group as substituent, C$_6$–C$_{15}$-aryl or arylalkyl or Si(R$^{11}$)$_3$ where R$^{11}$ is C$_1$–C$_{10}$-alkyl, C$_6$–C$_{15}$-aryl or C$_3$–C$_{10}$-cycloalkyl.

Very particular preference is given to those tin compounds II in which R$^1$, R$^3$, R$^4$, R$^6$, R$^8$ are hydrogen and R$^2$, R$^5$ are identical and are methyl, ethyl, n-propyl, in particular tert-butyl.

The tin compounds of the present invention are usually obtained by reacting a cyclopentadiene derivative III where R$^1$ to R$^8$ are hydrogen, C$_1$–C$_{10}$-alkyl, 5- to 7-membered cycloalkyl, which may in turn bear a C$_1$–C$_{10}$-alkyl group as substituent, C$_6$–C$_{15}$-aryl or arylalkyl where two adjacent radicals may also together form a cyclic group having from 4 to 15 carbon atoms, or Si(R$^{11}$)$_3$ where R$^{11}$ is C$_1$–C$_{10}$-alkyl, C$_6$–C$_{15}$-aryl or C$_3$–C$_{10}$-cycloalkyl, R$^9$ is

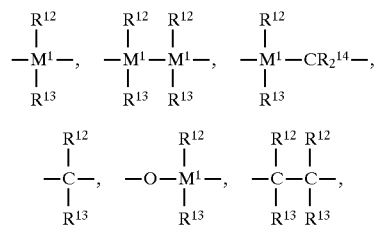

=BR$^{12}$, =AlR$^{12}$, —Ge—, —O—, —S—, =SO, =SO$_2$, =NR$^{12}$, =CO, =PR$^{12}$ or =P(O)R$^{12}$, where R$^{12}$, R$^{13}$ and R$^{14}$ are identical or different and are each a hydrogen atom, a halogen atom, a C$_1$–C$_{10}$-alkyl group, a C$_1$–C$_{10}$-fluoroalkyl group, a C$_6$–C$_{10}$-fluoroaryl group, a C$_6$–C$_{10}$-aryl group, a C$_1$–C$_{10}$-alkoxy group, a C$_2$–C$_{10}$-alkenyl group, a C$_7$–C$_{40}$-arylalkyl group, a C$_8$–C$_{40}$-arylalkenyl group or a C$_7$–C$_{40}$-alkylaryl group or R$^{12}$ and R$^{13}$ or R$^{12}$ and R$^{14}$ in each case together with the atoms connecting them form a ring, and M$^1$ is silicon or germanium
with a tin tetraamide of the formula IV

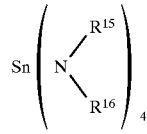

where R$^{15}$, R$^{16}$ are identical or different and are C$_1$–C$_{10}$-alkyl, C$_3$–C$_{10}$-cycloalkyl, C$_1$–C$_{10}$-fluoroalkyl, C$_6$–C$_{10}$-fluoroaryl, C$_6$–C$_{10}$-aryl, C$_7$–C$_{40}$-arylalkyl, C$_7$–C$_{40}$-alkylaryl.

This reaction is usually carried out in an organic solvent, preferably an ether such as diethyl ether or tetrahydrofuran, and at from −78° to 100° C., preferably from 0° to 60° C. The molar ratio of III to tin tetraamide IV is usually in the range from 3:1 to 1:3, preferably 2:1.

The synthesis of the virtually meso-free racemic ansa-metallocene I is usually carried out by reacting the above-defined tin compounds II with, preferably, metal halides, i.e. fluorides, bromides, iodides, preferably chlorides, of the metals titanium, zirconium, hafnium, vanadium, niobium or tantalum, preferably zirconium. In a well suited process, the metal halide, preferably chloride, is suspended in an organic solvent, preferably an aromatic or aliphatic hydrocarbon or an ether, i.e. toluene, heptane or tetrahydrofuran, and the tin compound II, preferably dissolved in the solvents mentioned, is added at from −78° to +150° C., preferably from 0° to 100° C. The molar ratio of transition metal halide:tin compound II is usually in the range from 3:1 to 1:3, preferably from 2:1 to 1:2, in particular 2:1.

The process of the present invention gives virtually "meso-free" racemic ansa-metallocene complexes I. The analysis for the meso and racemic forms was carried out by means of 1 H- and/or 13C-NMR spectroscopy.

The racemic ansa-metallocenes I obtainable by the process of the present invention can be used as catalysts or as constituents of catalyst systems, preferably in olefin polymerization.

EXAMPLES

Example 1

Synthesis of rac-4,4'-spirobis(8-sila-4-stanna-indacene)

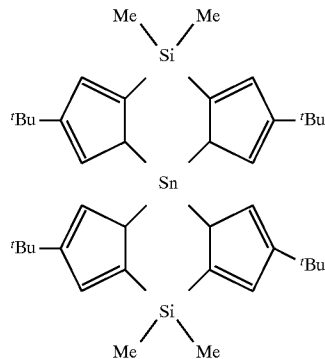

1.0 ml of $Sn(NMe_2)_4$ (6 mmol) was dissolved in 50 ml of ether. This ether solution of tetrakis(dimethylamino)tin was added dropwise over a period of 30 minutes to a solution of 3.3 g of dimethylbis(3-tert-butylcyclopentadienyl)silane (11 mmol) and 100 ml of ether. During the addition, the solution became golden yellow and dimethylamine was given off from the reaction mixture. The reaction mixture was left stirring overnight and the solvent volume was then reduced by about 80 ml under reduced pressure at room temperature. Stirring was continued until the tetrakis(dimethylamino)tin could no longer be detected by NMR spectroscopy. The solvent was then completely removed and the residue was admixed with pentane. A pale yellow precipitate consisting of rac-4,4'-spirobis(8-sila-4-stanna-indacene) was formed. This precipitate was separated from the solution by filtration and was washed with a little cold pentane. Evaporation of the solution led to renewed crystallization. Crystals suitable for X-ray analysis were obtained by crystallization from ether.

$MW(C_{40}H_{60}Si_2Sn)$: 715.8 g/mol

Yield: 2.91 g(4.1 mmol)74%

Table for Example 1: Data for the spiro compound

H—NMR: $CDCl_3$, internal standard: $CHCl_3$ (7.24 ppm), 298 K, 660 MHz

| Chemical shift δ (ppm) | Multiplicity | Number of H atoms | Assignment |
|---|---|---|---|
| 7.04 | s | 4 | ring H(1), $sp^2$, $^1H$—Sn coupling constant: 17 Hz |
| 6.12 | s | 4 | ring H(3), $sp^2$, $^1H$—Sn coupling constant: 9 Hz |
| 3.50 | s | 4 | ring H(3a), $sp^3$, $^1H$—Sn coupling constant: 103 Hz |
| 1.23 | s | 4 | $CMe_3$ |
| 0.37 | s | 12 | $CH_3$—Si |

$^{13}C$—NNR: $CDCl_3$ internal standard: $CDCl_3$ (77 ppm), 298 K, 150 MHz

| Chemical shift δ (ppm) | Number of C atoms | Assignment |
|---|---|---|
| 154.2 | 4 | ring C(2), $sp^2$ |
| 145.2 | 4 | ring C (7a), $sp^2$ |
| 137.4 | 4 | ring C(1), $sp^2$ |
| 126.6 | 4 | ring C(3), $sp^2$ |
| 58.9 | 4 | ring C(3a), $sp^3$ $^1J(Sn—^{13}C)$ coupling constant: 90 Hz |
| 32.1 | 4 | $CMe_3$ |
| 31.0 | 12 | $CMe_3$ |
| −2.2 | 4 | Si—$CH_3$ |

Example 2

Preparation of rac-dimethylsilanediylbis(3-tert-butylcyclopentadienyl)zirconium dichloride

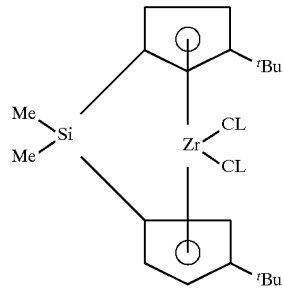

0.4 g of ZrCl$_4$ (1.72 mmol) was suspended in 200 ml of toluene. While stirring, a solution of 0.62 g of rac-4,4'-spirobis(8-sila-4-stanna-indacene) (0.86 mmol) in 250 ml of toluene was then added dropwise. The intense yellow solution formed was stirred overnight and the solvent was then removed under reduced pressure and replaced by 200 ml of pentane. The solution was then separated from any insoluble residue present and the solvent was again removed at room temperature. This procedure also simultaneously removed the tin tetrachloride formed. Pure rac-zirconocene remained.

MW (C$_{20}$H$_{30}$Cl$_2$SiZr): 460.7 g/mol

Yield: 0.64 g(1.39 mmol), 80% based on ZrCl$_4$

We claim:

1. A process for preparing racemic ansa-metallocene complexes of the formula I

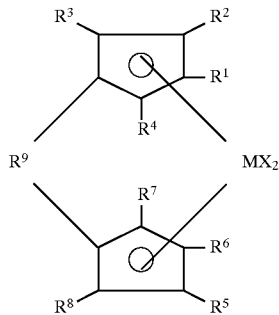

where the substituents and indices have the following meanings:

M is titanium, zirconium, hafnium, vanadium, niobium or tantalum,

X is fluorine, chlorine, bromine, iodine, hydrogen, C$_1$–C$_{10}$-alkyl, C$_6$–C$_{15}$-aryl or —OR$^{10}$, where R$^{10}$ is C$_1$–C$_{10}$-alkyl, C$_6$–C$_{15}$-aryl, alkylaryl, arylalkyl, fluoroalkyl or fluoroaryl each having from 1 to 10 carbon atoms in the alkyl radical and from 6 to 20 carbon atoms in the aryl radical, R$^1$ to R$^8$ are hydrogen, C$_1$–C$_{10}$-alkyl, 5- to 7-membered cycloalkyl which may in turn bear a C$_1$–C$_{10}$-alkyl group as substituent, C$_6$–C$_{15}$-aryl or arylalkyl, where two adjacent radicals may also together form a cyclic group having from 4 to 15 carbon atoms, or Si(R$^{11}$)$_3$ where R$^{11}$ is C$_1$–C$_{10}$-alkyl, C$_6$–C$_{15}$-aryl or C$_3$–C$_{10}$-cycloalkyl, R$^9$ is

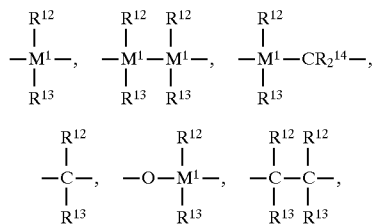

=BR$^{12}$, AlR$^{12}$, —Ge—, —O—, —S—, =SO, =SO$_2$, =NR$^{12}$, =CO, =PR$^{12}$ or =P(O)R$^{12}$, where R$^{12}$, R$^{13}$ and R$^{14}$ are identical or different and are each a hydrogen atom, a halogen atom, a C$_1$–C$_{10}$-alkyl group, a C$_1$–C$_{10}$-fluoroalkyl group, a C$_6$–C$_{10}$-fluoroaryl group, a C$_6$–C$_{10}$-aryl group, a C$_1$–C$_{10}$-alkoxy group, a C$_2$–C$_{10}$-alkenyl group, a C$_7$–C$_{40}$-arylalkyl group, a C$_8$–C$_{40}$-arylalkenyl group or a C$_7$–C$_{40}$-alkylaryl group or R$^{12}$ and R$^{13}$ or R$^{12}$ and R$^{14}$ in each case together with the atoms connecting them form a ring, and M$^1$ is silicon or germanium, by reacting a tin compound of the formula II

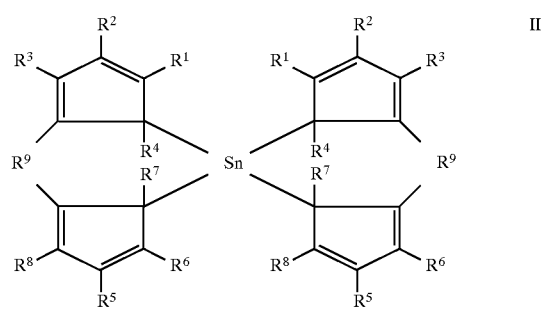

where

R$^1$ to R$^8$ are hydrogen, C$_1$–C$_{10}$-alkyl, 5- to 7-membered cycloalkyl which may in turn bear a C$_1$–C$_{10}$-alkyl group as substituent, C$_6$–C$_{15}$-aryl or arylalkyl, where two adjacent radicals may also together form a cyclic group having from 4 to 15 carbon atoms, or Si(R$^{11}$)$_3$ where R$^{11}$ is C$_1$–C$_{10}$-alkyl, C$_6$–C$_{15}$-aryl or C$_3$–C$_{10}$-cycloalkyl, R$^9$ is

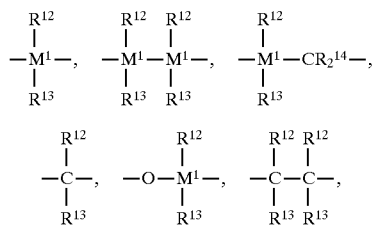

=BR$^{12}$, =AlR$^{12}$, —Ge—, —O—, —S—, =SO, =S$_2$, =NR$^{12}$, =CO, =PR$^{12}$ or =P(O)R$^{12}$, where R$^{12}$, R$^{13}$ and R$^{14}$ are identical or different and are each a hydrogen atom, a halogen atom, a C$_1$–C$_{10}$-alkyl group, a C$_1$–C$_{10}$-fluoroalkyl group, a C$_6$–C$_{10}$-fluoroaryl group, a C$_6$–C$_{10}$-aryl group, a C$_1$–C$_{10}$-alkoxy group, a C$_2$–C$_{10}$-alkenyl group, a C$_7$–C$_{40}$-arylalkyl group, a C$_8$–C$_{40}$-arylalkenyl group or a C$_7$–C$_{40}$-alkylaryl group or R$^{12}$ and R$^{13}$ or R$^{12}$ and R$^{14}$ in each case together with the atoms connecting them form a ring, and M¹ is silicon or germanium,
with a transition metal compound of the formula $MX_n$
where
- M is titanium, zirconium, hafnium, vanadium, niobium or tantalum,
- X is fluorine, chlorine, bromine, iodine or $-OR^{10}$,
  where $R^{10}$ is $C_1$–$C_{10}$-alkyl, $C_6$–$C_{15}$-aryl, alkylaryl, arylalkyl, fluoroalkyl or fluoroaryl each having from 1 to 10 carbon atoms in the alkyl radical and from 6 to 20 carbon atoms in the aryl radical,
- n is an integer from 3 to 5.

2. A process as claimed in claim 1, wherein the substituents $R^2$ and $R^5$ are identical or different and are $C_1$–$C_{10}$-alkyl, 5- to 7-membered cycloalkyl which in turn may bear a $C_1$–$C_{10}$-alkyl group as substituent, $C_6$–$C_{15}$-aryl or arylalkyl, or $Si(R^{11})_3$ where $R^{11}$ is $C_1$–$C_{10}$-alkyl $C_6$–$C_{15}$-aryl or $C_3$–$C_{10}$-cycloalkyl.

3. A process as claimed in claim 1, wherein $R^9$ is

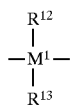

where $R^{12}$ and $R^{13}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ together with the atoms connecting them form a ring, and M¹ is silicon.

4. A process as claimed in claim 1, wherein the tin compound II is in the racemic form.

5. A tin compound of the formula II

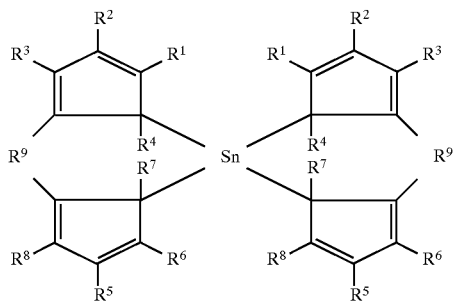

where
- $R^1$ to $R^8$ are hydrogen, $C_1$–$C_{10}$-alkyl, 5- to 7-membered cycloalkyl which may in turn bear a $C_1$–$C_{10}$-alkyl group as substituent, $C_6$–$C_{15}$-aryl or arylalkyl, where two adjacent radicals may also together form a cyclic group having from 4 to 15 carbon atoms, or $Si(R^{11})_3$ where
  - $R^{11}$ is $C_1$–$C_{10}$-alkyl, $C_6$–$C_{15}$-aryl or $C_3$–$C_{10}$-cycloalkyl,
- $R^9$ is

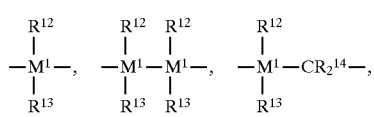

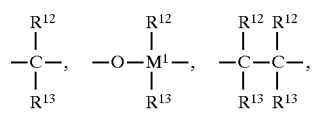

$=BR^{12}$, $=AlR^{12}$, $-Ge-$, $-O-$, $-S-$, $=SO$, $=SO_2$, $=NR^{12}$, $=CO$, $=PR^{12}$ or $=P(O)R^{12}$, where $R^{12}$, $R^{13}$ and $R^{14}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ or $R^{12}$ and $R^{14}$ in each case together with the atoms connecting them form a ring, and M¹ is silicon or germanium.

6. A tin compound as claimed in claim 5, wherein the substituents $R^2$ and $R^5$ are identical or different and are $C_1$–$C_{10}$-alkyl, 5- to 7-membered cycloalkyl which may in turn bear a $C_1$–$C_{10}$-alkyl group as substituent, $C_6$–$C_{15}$-aryl or arylalkyl, or $Si(R^{11})_3$ where $R^{11}$ is $C_1$- to $C_{10}$-alkyl, $C_6$–$C_{15}$-aryl or $C_3$–$C_{10}$-cycloalkyl.

7. A tin compound II as claimed in claim 5, wherein $R^9$ is

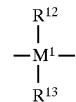

where $R^{12}$ and $R^{13}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ together with the atoms connecting them form a ring, and M¹ is silicon.

8. A tin compound II as claimed in claim 5 which is in the racemic form.

9. A process for preparing tin compounds of the formula II

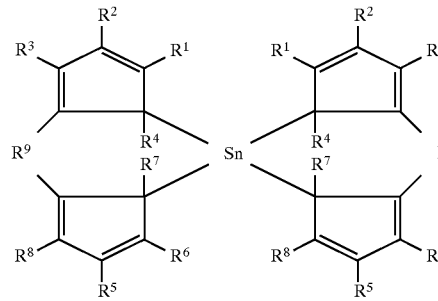

where
- $R^1$ to $R^8$ are hydrogen, $C_1$–$C_{10}$-alkyl, 5- to 7-membered cycloalkyl which may in turn bear a $C_1$–$C_{10}$-alkyl group as substituent, $C_6$–$C_{15}$-aryl or arylalkyl, where two adjacent radicals may also together form a cyclic group having from 4 to 15 carbon atoms, or $Si(R^{11})_3$ where
  - $R^{11}$ is $C_1$–$C_{10}$-alkyl, $C_6$–$C_{15}$-aryl or $C_3$–$C_{10}$-cycloalkyl, $R^9$ is

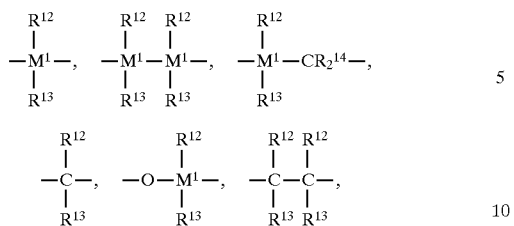

$=BR^{12}$, $=AlR^{12}$, —Ge—, —O—, —S—, $=SO$, $=SO_2$, $=NR^{12}$, $=CO$, $=PR^{12}$ or $=P(O)R^{12}$, where $R^{12}$, $R^{13}$ and $R^{14}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_2$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ or $R^{12}$ and $R^{14}$ in each case together with the atoms connecting them form a ring, and $M^1$ is silicon or germanium, by reacting a bridged cyclopentadiene derivative of the formula III

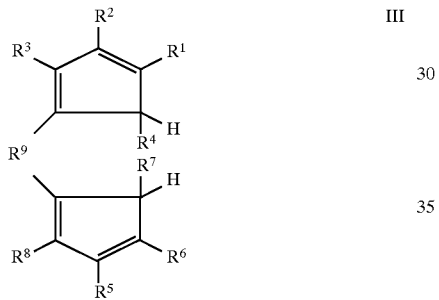

where $R^1$ to $R^8$ are hydrogen, $C_1$–$C_{10}$-alkyl, 5- to 7-membered cycloalkyl which in turn may bear a $C_1$–$C_{10}$-alkyl group as substituent, $C_6$–$C_{15}$-aryl or arylalkyl, where two adjacent radicals may also together form a cyclic group having from 4 to 15 carbon atoms, or $Si(R^{11})_3$ where $R^{11}$ is $C_1$–$C_{10}$-alkyl, $C_6$–$C_{15}$-aryl or $C_3$–$C_{10}$-cycloalkyl, $R^9$ is

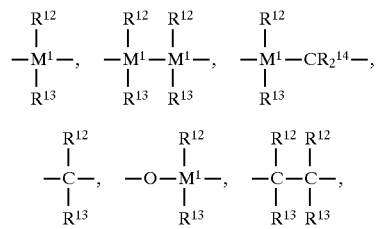

$=BR^{12}$, $AlR^{12}$, —Ge—, —O—, —S—, $=SO$, $=SO_2$, $=NR^{12}$, $=CO$, $=PR^{12}$ or $=P(O)R^{12}$, where $R^{12}$, $R^{13}$ and $R^{14}$ are identical or different and are each a hydrogen atom, a halogen atom, a $C_1$–$C_{10}$-alkyl group, a $C_1$–$C_{10}$-fluoroalkyl group, a $C_6$–$C_{10}$-fluoroaryl group, a $C_6$–$C_{10}$-aryl group, a $C_1$–$C_{10}$-alkoxy group, a $C_1$–$C_{10}$-alkenyl group, a $C_7$–$C_{40}$-arylalkyl group, a $C_8$–$C_{40}$-arylalkenyl group or a $C_7$–$C_{40}$-alkylaryl group or $R^{12}$ and $R^{13}$ or $R^{12}$ and $R^{14}$ in each case together with the atoms connecting them form a ring, and $M^1$ is silicon or germanium, with a tin tetraamide of the formula IV

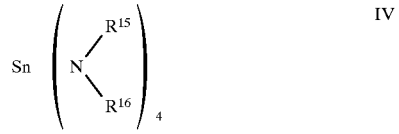

where $R^{15}$, $R^{16}$ are identical or different and are $C_1$–$C_{10}$-alkyl, $C_3$–$C_{10}$-cycloalkyl, $C_1$–$C_{10}$-fluoroalkyl, $C_6$–$C_{10}$-fluoroaryl, $C_6$–$C_{10}$-aryl, $C_7$–$C_{40}$-arylalkyl or $C_7$–$C_{40}$-alkylaryl.

* * * * *

UNITED STATES PATENT AND TRADEMARK OFFICE
CERTIFICATE OF CORRECTION

PATENT NO.: 5,892,081

DATED: April 6, 1999

INVENTOR(S): SUELING et al.

It is certified that error appears in the above-identified patent and that said Letters Patent is hereby corrected as shown below:

Col. 20, claim 1, line 58, "$=S_2$," should be -- $=SO_2$,--.

Col. 24, claim 9, line 24, "$C_1-C_{10}$-alkenyl group" should be --$C_2-C_{10}$-alkenyl group--.

Signed and Sealed this

Seventh Day of September, 1999

Attest:

Q. TODD DICKINSON

Attesting Officer

Acting Commissioner of Patents and Trademarks